US012558068B2

(12) United States Patent
Usuda

(10) Patent No.: US 12,558,068 B2
(45) Date of Patent: Feb. 24, 2026

(54) MEDICAL IMAGE PROCESSING APPARATUS, ENDOSCOPE SYSTEM, MEDICAL IMAGE PROCESSING METHOD, AND MEDICAL IMAGE PROCESSING PROGRAM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 157 days.

(21) Appl. No.: 18/468,744

(22) Filed: Sep. 18, 2023

(65) Prior Publication Data

US 2024/0000432 A1     Jan. 4, 2024

Related U.S. Application Data

(63) Continuation of application No. PCT/JP2022/010893, filed on Mar. 11, 2022.

(30) Foreign Application Priority Data

Mar. 22, 2021     (JP) .................................. 2021-047137

(51) Int. Cl.
   *G06T 7/70*         (2017.01)
   *A61B 8/00*         (2006.01)
                       (Continued)

(52) U.S. Cl.
   CPC ................ *A61B 8/469* (2013.01); *A61B 8/12* (2013.01); *A61B 8/463* (2013.01); *A61B 8/54* (2013.01);
                       (Continued)

(58) Field of Classification Search
   CPC ...................... G06V 10/25; G06T 2207/10068
                       (Continued)

(56) References Cited

U.S. PATENT DOCUMENTS 11,464,394 B2    10/2022    Endo
11,900,615 B2    2/2024    Ishikake
                 (Continued)

FOREIGN PATENT DOCUMENTS

JP        2017158892        9/2017
JP        2020069300        5/2020
                 (Continued)

OTHER PUBLICATIONS

Li et al., Multi-Task Refined Boundary-Supervision U-Net (MRBSU-Net) for Gastrointestinal Stromal Tumor Segmentation in endoscopic Ultrasound (EUS) Images, Digital Object Identifier 10.1109/ACCESS.2019.2963472, vol. 8, 2020, pp. 5806-5816.*
                 (Continued)

*Primary Examiner* — Samantha (Yuehan) Wang
(74) *Attorney, Agent, or Firm* — JCIPRNET

(57)         ABSTRACT

A medical image processing apparatus includes a processor configured to execute an image acquisition process for sequentially acquiring time-series medical images; a region-of-interest recognition process for recognizing a position and a type of a region of interest from the medical images; and a display control process for causing a display device to display position information indicating the position of the region of interest and type information indicating the type of the region of interest such that the position information and the type information are superimposed on the medical images. In the display control process, the processor changes a position at which the position information is to be displayed according to a change in the position of the region of interest over time, and maintains a position at which the type information is to be displayed regardless of a change in the position of the region of interest over time.

13 Claims, 9 Drawing Sheets

(51) Int. Cl.

| | |
|---|---|
| *A61B 8/12* | (2006.01) |
| *G06T 11/60* | (2006.01) |
| *G06V 10/25* | (2022.01) |
| *G06V 10/764* | (2022.01) |
| *G06V 20/50* | (2022.01) |

(52) U.S. Cl.

CPC ................ *G06T 7/70* (2017.01); *G06T 11/60* (2013.01); *G06V 10/25* (2022.01); *G06V 10/764* (2022.01); *G06V 20/50* (2022.01); *G06T 2207/10068* (2013.01); *G06T 2207/10132* (2013.01); *G06T 2207/30092* (2013.01); *G06V 2201/031* (2022.01)

(58) Field of Classification Search

USPC .......................................................... 345/629

See application file for complete search history.

(56) References Cited

U.S. PATENT DOCUMENTS

| | | | |
|---|---|---|---|
| 2020/0320702 | A1 | 10/2020 | Kamon |
| 2021/0042553 | A1 | 2/2021 | Oosake |
| 2021/0366110 | A1 | 11/2021 | Oosake et al. |
| 2023/0016855 | A1 | 1/2023 | Endo |
| 2023/0086972 | A1 | 3/2023 | Kamon |
| 2023/0199152 | A1 | 6/2023 | Oosake |

FOREIGN PATENT DOCUMENTS

| | | | | |
|---|---|---|---|---|
| JP | 2021037036 | | 3/2021 | |
| WO | 2019138773 | | 7/2019 | |
| WO | 2019220916 | | 11/2019 | |
| WO | 2020170809 | | 8/2020 | |
| WO | 2020183770 | | 9/2020 | |
| WO | WO-2020183770 | A1 * | 9/2020 | ......... A61B 1/00006 |
| WO | 2020194663 | | 10/2020 | |

OTHER PUBLICATIONS

Xinyi Li et al., "Multi-Task Refined Boundary-Supervision U-Net (MRBSU-Net) for Gastrointestinal Stromal Tumor Segmentation in Endoscopic Ultrasound (EUS) Images", IEEE Engineering in Medicine and Biology Society Section, Jan. 1, 2020, pp. 5805-5816.

"Search Report of Europe Counterpart Application", issued on Aug. 8, 2024, p. 1-p. 11.

"International Search Report (Form PCT/ISA/210) of PCT/JP2022/010893", mailed on May 31, 2022, with English translation thereof, pp. 1-5.

"Written Opinion of the International Searching Authority (Form PCT/ISA/237) of PCT/JP2022/010893", mailed on May 31, 2022, with English translation thereof, pp. 1-8.

"Notice of Reasons for Refusal of Japan Counterpart Application", issued on Sep. 3, 2025, with English translation thereof, p. 1-p. 8.

* cited by examiner

FIG. 4

Settings of Display Style

| Display Format of Position Information | ⦿ Cross |
| | ○ Name of Organ, etc. |
| | ○ Initial(s) of Organ, etc. |

| Color of Position Information | Blue ▼ |

| Color of Type Information | Yellow ▼ |

| View List of Regions of Interest | ⦿ On    ○ Off |

| Change Highlighting Level in List View | ⦿ On    ○ Off |

| Method of Changing Highlighting Level | Gray out ▼ |

| Leader Line | ○ Yes    ⦿ No |

OK              Cancel

MEDICAL IMAGE PROCESSING APPARATUS, ENDOSCOPE SYSTEM, MEDICAL IMAGE PROCESSING METHOD, AND MEDICAL IMAGE PROCESSING PROGRAM

CROSS-REFERENCE TO RELATED APPLICATIONS

The present application is a Continuation of PCT International Application No. PCT/JP2022/010893 filed on Mar. 11, 2022 claiming priority under 35 U.S.C. § 119(a) to Japanese Patent Application No. 2021-047137 filed on Mar. 22, 2021. Each of the above applications is hereby expressly incorporated by reference, in its entirety, into the present application.

BACKGROUND OF THE INVENTION

1. Field of the Invention

The present invention relates to a medical image processing apparatus, an endoscope system, a medical image processing method, and a medical image processing program, and more specifically to a technique for displaying a recognition result of a region of interest.

2. Description of the Related Art

It is known to notify a user such as a doctor of a recognition result of a region of interest, which is obtained by a medical image processing apparatus, to assist the user in observing a medical image or making a diagnosis. For example, JP2020-069300A describes display of a bounding box or the like at the position of a recognized region of interest. JP2020-069300A also describes display of text, indicating the types of a region of interest, outside an image area.

SUMMARY OF THE INVENTION

During observation using a medical apparatus such as an endoscope apparatus or an ultrasound apparatus, a doctor operates the apparatus while checking organs, blood vessels, and the like (regions of interest or anatomical regions) on a screen so that a desired region appears on the screen, which is a very difficult operation. To simplify the operation of the apparatus, it is considered to detect an organ, a blood vessel, or the like by using image recognition technology such as AI (Artificial Intelligence) and present the detected organ, blood vessel, or the like to the user (for example, display a recognition result on the screen). Such display is preferably turned on or off freely at the user's discretion. However, depending on the type of medical apparatus, the user may operate the medical apparatus with both hands. Thus, the user is not always able to turn on or off the display through their operation. It is therefore preferable that the display of a recognition result support and not interfere with the user's observation. In the existing technique described above, as in JP2020-069300A, however, a recognition result of a region of interest is difficult to appropriately display.

The present invention has been made in view of such circumstances, and an object thereof is to provide a medical image processing apparatus, an endoscope system, a medical image processing method, and a medical image processing program that can appropriately display a recognition result of a region of interest.

To achieve the object described above, a medical image processing apparatus according to a first aspect of the present invention is a medical image processing apparatus including a processor configured to execute an image acquisition process for sequentially acquiring time-series medical images; a region-of-interest recognition process for recognizing a position and a type of a region of interest from the medical images; and a display control process for causing a display device to display position information indicating the position of the region of interest and type information indicating the type of the region of interest such that the position information and the type information are superimposed on the medical images. The processor is configured to, in the display control process, change a position at which the position information is to be displayed in accordance with a change in the position of the region of interest over time, and maintain a position at which the type information is to be displayed regardless of a change in the position of the region of interest over time.

A conceivable example of a method for displaying a recognition result of a region of interest in medical images is to display position information indicating the position of the region of interest and type information such as the name of the region of interest. Since the position of the region of interest in the medical images changes with the progress of observation (with the passage of time), if a display position at which the type information is to be displayed is changed in accordance with a change in the position of the region of interest, a large change in the position of the region of interest causes a large change in the display position of the type information, resulting in reduced visibility. If the display position of the position information is maintained regardless of a change in the position of the region of interest, in contrast, the position of the region of interest fails to be displayed correctly.

In view of this, the medical image processing apparatus according to the first aspect can support the user's observation by displaying the position information and the type information, with the display of the position information and the type information being less likely to interfere with the user's observation.

As described above, according to the first aspect, a recognition result of a region of interest can be appropriately displayed. In the first aspect, for some regions of interest, the display positions of not only the position information but also the type information may be changed with a change in the positions of the regions of interest, and for other regions of interest, the display positions of the type information may be maintained regardless of a change in the positions of the regions of interest. Further, whether to change the display position of the type information with a change in the position of the region of interest may be set in accordance with the type of the region of interest (the characteristics of the anatomical region).

In the first aspect, the type of the region of interest is, for example, but not limited to, the name of an organ or a blood vessel, or a classification result of a lesion. In the first aspect, a detector constructed by machine learning may be used to recognize the region of interest.

In the first aspect and the following aspects, the phrase "acquiring time-series medical images" includes sequentially acquiring a plurality of medical images captured at a determined frame rate. The acquisition may or may not be performed in real time. For example, medical images captured and recorded in advance may be acquired.

The medical image processing apparatus according to the first aspect can be implemented as, for example, a processor section of a medical image processing system, but is not limited to this aspect. The term "medical image" refers to an image obtained as a result of imaging, measurement, or the like of a living body such as a human body for the purpose of diagnosis, treatment, measurement, or the like. Examples of the medical image include an endoscopic image, an ultrasound image, a CT image (CT: Computed Tomography), and an MRI image (MRI: Magnetic Resonance Imaging). The medical image is also referred to as an image for medical use. In the first aspect and the following aspects, the term "region of interest (ROI)" may be a lesion region, a candidate lesion region, an organ, a vessel, a region after treatment, a treatment tool, or the like in a medical image. The "region of interest" may be referred to as an "interested region".

A medical image processing apparatus according to a second aspect is the medical image processing apparatus according to the first aspect, in which the processor is configured to, in the display control process, cause a geometric shape or a text to be displayed as the position information at the position of the region of interest in the medical images. The second aspect defines a specific aspect of the position information.

A medical image processing apparatus according to a third aspect is the medical image processing apparatus according to the first or second aspect, in which the processor is configured to, in the display control process, cause a text indicating the type of the region of interest to be displayed as the type information. The third aspect defines a specific aspect of the type information.

A medical image processing apparatus according to a fourth aspect is the medical image processing apparatus according to any one of the first to third aspects, in which the processor is configured to cause a geometric shape or a text set in accordance with the type of the region of interest to be displayed as the position information. The fourth aspect defines a specific aspect of the position information. Displaying position information corresponding to the type of the region of interest allows the user to easily grasp the recognition result of the region of interest.

A medical image processing apparatus according to a fifth aspect is the medical image processing apparatus according to any one of the first to fourth aspects, in which the processor is configured to, in the display control process, cause the position information to be displayed in association with the type information. According to the fifth aspect, the user can easily grasp the relationship between the position information and the type information.

A medical image processing apparatus according to a sixth aspect is the medical image processing apparatus according to any one of the first to fifth aspects, in which the processor is configured to, in the display control process, cause a line segment having one endpoint at the position of the region of interest and another endpoint at a position of the type information to be displayed as the position information. According to the sixth aspect, the user can easily grasp the relationship between the position information and the type information.

A medical image processing apparatus according to a seventh aspect is the medical image processing apparatus according to any one of the first to sixth aspects, in which the processor is configured to, in the display control process, cause the type of the region of interest recognized in the region-of-interest recognition process to be displayed as the type information. In the seventh aspect, the "type of the region of interest recognized in the region-of-interest recognition process" means the type of a region of interest that is actually recognized.

A medical image processing apparatus according to an eighth aspect is the medical image processing apparatus according to any one of the first to sixth aspects, in which the processor is configured to, in the display control process, cause the type of the region of interest recognizable in the region-of-interest recognition process to be displayed as the type information. In the eighth aspect, the "type of the region of interest recognizable in the region-of-interest recognition process" means the type of a region of interest that is not actually recognized but is likely to be recognized. The "type of the recognizable region of interest" may differ depending on the type of the medical apparatus or the configuration of the recognizer.

A medical image processing apparatus according to a ninth aspect is the medical image processing apparatus according to the eighth aspect, in which the processor is configured to cause the type information indicating a region of interest that is not actually recognized among regions of interest recognizable in the region-of-interest recognition process to be displayed with a second notification level lower than a first notification level for the type information indicating a region of interest that is actually recognized in the region-of-interest recognition process. If the types of all of the recognizable regions of interest are displayed with the same notification level, it may be difficult for the user to grasp the type of an actually recognized region of interest. Accordingly, as in the ninth aspect, changing the notification level allows the user to easily grasp the type of an actually recognized region of interest.

A medical image processing apparatus according to a tenth aspect is the medical image processing apparatus according to any one of the first to ninth aspects, in which the processor is configured to, in the display control process, cause the position information to be displayed within an image signal display area in the medical images, and cause the type information to be displayed outside the image signal display area in the medical images.

To achieve the object described above, an endoscope system according to an eleventh aspect of the present invention includes the medical image processing apparatus according to any one of the first to tenth aspects, an endoscope to be inserted into a subject, the endoscope including an imaging unit configured to sequentially capture the medical images; and the display device. The endoscope system according to the eleventh aspect includes the medical image processing apparatus according to any one of the first to tenth aspects, and thus can appropriately display a recognition result of a region of interest.

An endoscope system according to a twelfth aspect is the endoscope system according to the eleventh aspect, in which the endoscope is an ultrasonic endoscope configured to acquire ultrasound images of the subject as the medical images.

To achieve the object described above, a medical image processing method according to a thirteenth aspect of the present invention is a medical image processing method executed by a medical image processing apparatus including a processor, the processor being configured to execute an image acquisition step of sequentially acquiring time-series medical images; a region-of-interest recognition step of recognizing a position and a type of a region of interest from the medical images; and a display control step of causing a display device to display position information indicating the position of the region of interest and type information indicating the type of the region of interest such that the position information and the type information are superimposed on the medical images. The processor is configured to, in the display control step, change a position at which the position information is to be displayed in accordance with a change in the position of the region of interest over time, and maintain a position at which the type information is to be displayed regardless of a change in the position of the region of interest over time. According to the thirteenth aspect, as in the first aspect, recognition result of a region of interest can be appropriately displayed. The medical image processing method according to the thirteenth aspect may further execute processing similar to that of the second to tenth aspects.

To achieve the object described above, a medical image processing program according to a fourteenth aspect of the present invention is a medical image processing program for causing a medical image processing apparatus including a processor to execute a medical image processing method. The medical image processing method includes an image acquisition step of sequentially acquiring time-series medical images; a region-of-interest recognition step of recognizing a position and a type of a region of interest from the medical images; and a display control step of causing a display device to display position information indicating the position of the region of interest and type information indicating the type of the region of interest such that the position information and the type information are superimposed on the medical images. In the display control step, a position at which the position information is to be displayed is changed in accordance with a change in the position of the region of interest over time, and a position at which the type information is to be displayed i s maintained regardless of a change in the position of the region of interest over time. According to the fourteenth aspect, as in the first aspect, recognition result of a region of interest can be appropriately displayed. The medical image processing program according to the fourteenth aspect may be a program for further executing processing similar to that of the second to tenth aspects. Aspects of the present invention can also provide a non-transitory recording medium storing the computer-readable code of the program according to these aspects.

As described above, a medical image processing apparatus, an endoscope system, a medical image processing method, and a medical image processing program according to the present invention can provide an appropriate notification of a recognition result of a region of interest.

BRIEF DESCRIPTION OF THE DRAWINGS

FIG. 4 is a view illustrating an example of a screen for setting a display style;

DESCRIPTION OF THE PREFERRED EMBODIMENTS

Embodiments of a medical image processing apparatus, an endoscope system, a medical image processing method, and a medical image processing program according to the present invention will be described hereinafter in detail with reference to the accompanying drawings.

First Embodiment

Figure 1:
FIG. 1 is an external view of an endoscope system according to a first embodiment.

Overall Configuration of Endoscope System Including Medical Image Processing Apparatus FIG. 1 is an external view of an endoscope system according to a first embodiment. As illustrated in FIG. 1, an endoscope system 2 (endoscope system, medical imaging apparatus) includes an ultrasound scope 10 (endoscope, ultrasonic endoscope), an ultrasonic processor device 12 (medical image processing apparatus) that generates an ultrasound image (medical image), an endoscope processor device 14 (medical image processing apparatus) that generates an endoscopic image (medical image), a light source device 16 that supplies illumination light (observation light) to the ultrasound scope 10 to illuminate the inside of a body cavity, and a monitor 18 (display device) that displays the ultrasound image and the endoscopic image.

The ultrasound scope 10 includes an insertion section 20 to be inserted into a body cavity of a subject, a handheld operation section 22 coupled to a proximal end portion of the insertion section 20 and to be operated by an operator, and a universal cord 24 having one end connected to the handheld operation section 22. The other end of the universal cord 24 is provided with an ultrasonic connector 26 to be connected to the ultrasonic processor device 12, an endoscope connector 28 to be connected to the endoscope processor device 14, and a light source connector 30 to be connected to the light source device 16.

The ultrasound scope 10 is detachably connected to the ultrasonic processor device 12, the endoscope processor device 14, and the light source device 16 through these connectors. The light source connector 30 is also connected to an air/water supply tube 32 and a suction tube 34.

The light source device 16 is constituted by light sources for illumination (for example, a red light source, a green light source, a blue light source, and a violet light source that emit red, green, blue, and violet narrow-band light, respectively), a diaphragm, a condenser lens, a light source control unit, and so on, and these light sources can convert normal light (white light), special light (such as narrow-band light), and a combination thereof into observation light.

The monitor 18 receives respective video signals generated by the ultrasonic processor device 12 and the endoscope processor device 14 and displays an ultrasound image and an endoscopic image. The ultrasound image and the endoscopic image can be displayed such that only one of the images is appropriately switched and displayed on the monitor 18, or both of the images are simultaneously displayed.

The handheld operation section 22 is provided with an air/water supply button 36 and a suction button 38, which are arranged side by side, and is also provided with a pair of angle knobs 42 and a treatment tool insertion port 44.

The insertion section 20 has a distal end, a proximal end, and a longitudinal axis 20a. The insertion section 20 is constituted by a tip main body 50, a bending part 52, and an elongated long flexible soft part 54 in this order from the distal end side of the insertion section 20. The tip main body 50 is formed by a hard member. The bending part 52 is coupled to the proximal end side of the tip main body 50. The soft part 54 couples the proximal end side of the bending part 52 to the distal end side of the handheld operation section 22. That is, the tip main body 50 is disposed on the distal end side of the insertion section 20 in the longitudinal axis 20a. The bending part 52 is operated to bend by turning the pair of angle knobs 42 disposed in the handheld operation section 22. As a result, the user can direct the tip main body 50 in a desired direction.

The tip main body 50 is attached with an ultrasound probe 62 (imaging unit) and a bag-like balloon 64 that covers the ultrasound probe 62. The balloon 64 can expand or contract when water is supplied from a water supply tank 70 or the water in the balloon 64 is sucked by a suction pump 72. The balloon 64 is inflated until the balloon 64 abuts against the inner wall of the body cavity to prevent attenuation of an ultrasound wave and an ultrasound echo (echo signal) during ultrasound observation.

The tip main body 50 is also attached with an endoscopic observation portion (not illustrated) having an illumination portion and an observation portion including an objective lens, an imaging element, and so on. The endoscopic observation portion is disposed behind the ultrasound probe 62 (on the handheld operation section 22 side).

With the configuration described above, the endoscope system 2 can sequentially acquire (sequentially capture) endoscopic images (optical images) and ultrasound images. The endoscope system 2 may acquire endoscopic images or ultrasound images from a recording unit 120 or a server or a database (not illustrated).

Medical Image Processing Apparatus

Figure 2:
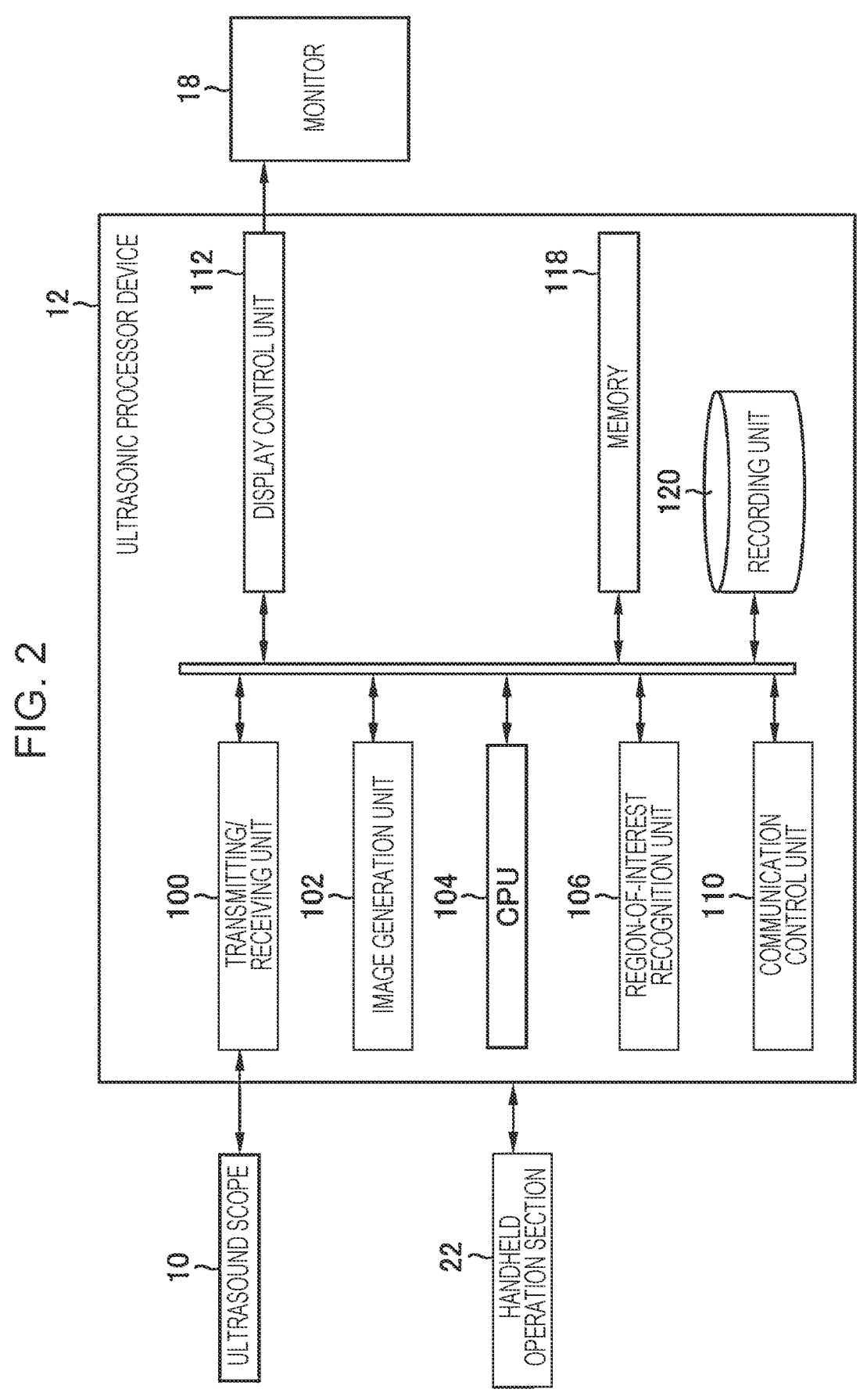
FIG. 2 is a diagram illustrating a configuration of a main part of an ultrasonic processor device.

FIG. 2 is a diagram illustrating a configuration of a main part of an ultrasonic processor device.

The ultrasonic processor device 12 (medical image processing apparatus, processor) illustrated in FIG. 2 is a device that recognizes a region of interest (target object) in a medical image on the basis of sequentially acquired time-series medical images and causes a display device to display a recognition result. The ultrasonic processor device 12 is constituted by a transmitting/receiving unit 100 (processor, image acquisition unit), an image generation unit 102 (processor, image acquisition unit), a CPU 104 (processor, CPU: Central Processing Unit), a region-of-interest recognition unit 106 (processor, region-of-interest recognition unit), a communication control unit 110 (processor), a display control unit 112 (processor, display unit), a memory 118, and the recording unit 120 (recording device). The processing of each of these components is implemented by one or more processors, as described below.

The CPU 104 operates in accordance with various programs stored in the memory 118 and including a medical image processing program according to the present invention to perform overall control of the region-of-interest recognition unit 106, the communication control unit 110, and the display control unit 112, and serves as some of these units. The memory 118 includes a non-transitory recording medium such as a ROM (ROM: Read Only Memory) on which the medical image processing program and so on are recorded, and a transitory recording medium such as a RAM (RAM: Random Access Memory) used as a temporary storage area.

The transmitting/receiving unit 100 and the image generation unit 102, which serve as an image acquisition unit, sequentially acquire time-series medical images (image acquisition process, image acquisition step).

A transmitting unit of the transmitting/receiving unit 100 generates a plurality of drive signals to be applied to a plurality of ultrasonic transducers of the ultrasound probe 62 of the ultrasound scope 10, and assigns respective delay times to the plurality of drive signals on the basis of a transmission delay pattern selected by a scan control unit (not illustrated) before applying the plurality of drive signals to the plurality of ultrasonic transducers.

A receiving unit of the transmitting/receiving unit 100 amplifies a plurality of detection signals, each of which is output from one of the plurality of ultrasonic transducers of the ultrasound probe 62, and converts the detection signals from analog detection signals to digital detection signals (also referred to as RF (Radio Frequency) data). The RF data is input to the image generation unit 102.

The image generation unit 102 assigns respective delay times to the plurality of detection signals represented by the RF data on the basis of a reception delay pattern selected by the scan control unit and adds the detection signals together to perform reception focus processing. Through the reception focus processing, sound ray data in which the focus of the ultrasound echo is narrowed is formed.

The image generation unit 102 corrects the sound ray data for attenuation caused by the distance in accordance with the depth of the reflection position of the ultrasound wave by using STC (Sensitivity Time Control), and then performs envelope detection processing on the sound ray data by using a low pass filter or the like to generate envelope data. The image generation unit 102 stores envelope data for one frame or more preferably for a plurality of frames in a cine memory (not illustrated). The image generation unit 102 performs pre-process processing, such as Log (logarithmic) compression and gain adjustment, on the envelope data stored in the cine memory to generate a B-mode image.

In this way, the transmitting/receiving unit 100 and the image generation unit 102 sequentially acquire time-series B-mode images (hereafter referred to as "medical images").

The region-of-interest recognition unit 106 performs a process (detection process, region-of-interest recognition process, region-of-interest recognition step) of recognizing information related to the position of a region of interest in a medical image on the basis of the medical images and a process (classification process, classification step) of classifying the region of interest into a class among a plurality of classes on the basis of the medical image. For example, the region-of-interest recognition unit 106 can be configured using a trained model constructed by machine learning (a model trained by using an image set constituted by captured images of a living body), such as a CNN (Convolutional Neural Network) or an SVM (Support Vector Machine). In the present embodiment, the region of interest is, for example, an organ or a blood vessel in a medical image (a tomographic image of a B-mode image), and examples of the region of interest include the pancreas, the main pancreatic duct, the spleen, the splenic vein, the splenic artery, and the gallbladder.

An example of a layer configuration of a CNN by which the region-of-interest recognition unit 106 is constituted will be described. The CNN includes an input layer, an intermediate layer, and an output layer. The input layer receives a medical image generated by the image generation unit 102 and outputs a feature value. The intermediate layer includes convolution layers and pooling layers and receives the feature value output from the input layer to calculate another feature value. These layers have a structure in which a plurality of "nodes" are connected by "edges", and hold a plurality of weight parameters. The values of the weight parameters change as learning progresses. The output layer recognizes a region of interest appearing in the input medical image on the basis of the feature value output from the intermediate layer and outputs the result.

In this example, when sequentially receiving time-series medical images, the region-of-interest recognition unit 106 recognizes (detects) the position of a region of interest in each of the received medical images, outputs information related to the position (position information), recognizes (classifies) a class to which the region of interest belongs among a plurality of classes, and outputs information (class information, type information) indicating the recognized class.

The display control unit 112 causes the monitor 18 (display device) to display the time-series medical images (endoscopic images, ultrasound images) sequentially acquired by the transmitting/receiving unit 100 and the image generation unit 102. In this example, a moving image indicating an ultrasound tomographic image is displayed on the monitor 18. The display control unit 112 further causes the monitor 18 to display a target object at a notification level determined by a notification level determination unit (not illustrated).

Medical image processing with the functions described above will be described in detail below.

Implementation of Functions by Various Processors

The functions of the ultrasonic processor device 12 described above can be implemented using various processors and a recording medium. The various processors include, for example, a CPU (Central Processing Unit), which is a general-purpose processor that executes software (program) to implement various functions. The various processors described above also include a GPU (Graphics Processing Unit), which is a processor specialized for image processing, and a programmable logic device (PLD) such as an FPGA (Field Programmable Gate Array), which is a processor whose circuit configuration is changeable after manufacture. A configuration using a GPU is effective for the processing of images as in the present invention. Further, a dedicated electric circuit or the like, which is a processor having a circuit configuration designed specifically for executing specific processing, such as an ASIC (Application Specific Integrated Circuit), is also included in the "various processors" described above.

The function of each component may be implemented by one processor or may be implemented by a plurality of processors of the same type or different types (for example, a plurality of FPGAs, a combination of a CPU and an FPGA, or a combination of a CPU and a GPU). Alternatively, a plurality of functions may be implemented by a single processor. Examples of configuring a plurality of functions by a single processor include, first, a form in which, as typified by a computer, the single processor is configured by a combination of one or more CPUs and software and the processor is implemented as the plurality of functions. The examples include, second, a form in which, as typified by a system on chip (SoC) or the like, a processor is used in which the functions of the entire system are implemented by a single IC (Integrated Circuit) chip. As described above, the various functions are configured using one or more of the various processors described above as a hardware structure. More specifically, the hardware structure of the various processors is an electric circuit (circuitry) including a combination of circuit elements such as semiconductor elements. These electric circuits may be electric circuits that implement the functions described above by using logical operations such as logical OR, logical AND, logical NOT, exclusive OR, and a combination thereof.

When the processor or electric circuit described above executes software (program), the code of the software to be executed, which is readable by a computer (for example, various processors or electric circuits constituting the ultrasonic processor device 12, and/or a combination thereof), is stored in a non-transitory recording medium such as a ROM (Read Only Memory), and the computer refers to the software. The software stored in the non-transitory recording medium includes a medical image processing program for executing a medical image processing method according to the present invention, and data used for the execution (such as data used to set a display style and a notification style, and weight parameters used in the region-of-interest recognition unit 106). The code may be recorded in a non-transitory recording medium such as various magneto-optical recording devices or a semiconductor memory, instead of the ROM. At the time of processing using software, for example, a RAM (RAM: Random Access Memory, memory) is used as a temporary storage area, and, for example, data stored in an EEPROM (Electrically Erasable and Programmable Read Only Memory) (not illustrated) can also be referred to. The "non-transitory recording medium" may be the memory 118 or the recording unit 120.

The recording unit 120 has recorded thereon an ultrasound image and an endoscopic image (medical image), a detection result of a region of interest, processing conditions (conditions for detection and providing a notification), and so on. Other information may also be recorded. The communication control unit 110 performs control to acquire a medical image and the like from another medical imaging apparatus connected to the endoscope system 2, an external server, or a database.

Procedure of Medical Image Processing

Figure 3:
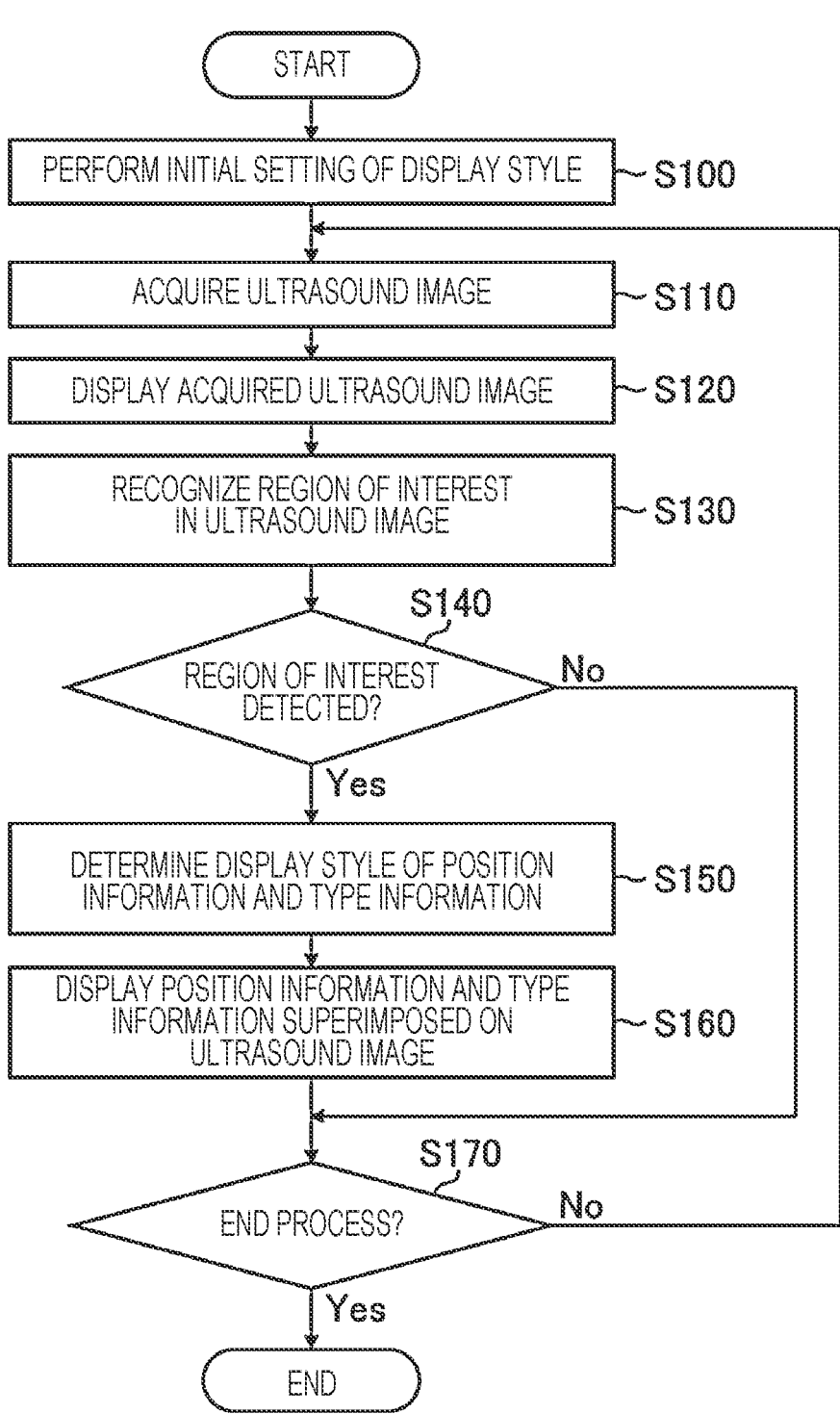
FIG. 3 is a flowchart illustrating a procedure of a medical image processing method according to the first embodiment.

Medical image processing performed in the endoscope system 2 having the configuration described above (execution of a medical image processing method and a medical image processing program according to the present invention) will be described. FIG. 3 is a flowchart illustrating a procedure of a medical image processing method according to the first embodiment. The procedures described below may be executed in a different order as necessary.

Initial Setting

The display control unit 112 (processor) sets conditions necessary to execute the medical image processing method/program in accordance with the user's operation through an operation section (such as a keyboard, a mouse, a touch panel, or a microphone) (not illustrated) and/or preset processing conditions (for example, default processing conditions) (step S100: initial setting step). For example, the display control unit 112 sets the display style (such as the type and color of a text or a symbol), the highlighting level, and the like of the position information and the type information. The user can set the processing conditions by, for example, turning on/off a radio button, making a selection in a pull-down menu, or performing other operation on a screen such as that in FIG. 4 (not all of the settings for the processing conditions are illustrated) through the operation section. The display control unit 112 can cause a display device such as the monitor 18 to display such a screen. The settings include, for example, what kind of geometric shape or text (type, color, and the like) to display the position information and the type information with, and whether to display a list of types of recognizable regions of interest. The display control unit 112 may set the processing conditions not only at the start of processing but also during the execution of the following steps.

Acquisition of Ultrasound Image and Recognition of Region of Interest

The transmitting/receiving unit 100 and the image generation unit 102 sequentially acquire time-series ultrasound images (medical images) (step S110: image acquisition process, image acquisition step). The display control unit 112 causes the monitor 18 to display an acquired ultrasound image (step S120: display control process, display control step). The region-of-interest recognition unit 106 recognizes the position and type of a region of interest in the ultrasound image (step S130: region-of-interest recognition process, region-of-interest recognition step). The region-of-interest recognition unit 106 can define, for example, the center position of a rectangular shape surrounding the region of interest as the position of the region of interest, and set information indicating the position (such as coordinates in the image) as the "position information". In this embodiment, information indicating a type of organ or blood vessel can be referred to as "class information or type information".

Superimposed Display of Position Information and Type Information

If the region-of-interest recognition unit 106 detects a region of interest (YES in step S140), the display control unit 112 determines the display style of the position information and the type information on the basis of the conditions set in step S100 (step S150: display control process, display control step). The display control unit 112 causes a display device (such as the monitor 18, the same applies hereinafter) to display the position information and the type information superimposed on the ultrasound image in the determined display style (step S160: display control process, display control step). For example, the display control unit 112 determines a display style such that "a cross (geometric shape; position information) is displayed superimposed at the center position of a rectangular shape surrounding the region of interest and the name of the actually recognized (detected) region of interest is displayed in text" and performs display in the determined display style. The processing of steps S110 to S160 is performed sequentially while time-series ultrasound images are acquired. The recognition of a region of interest and the display control process may be performed on all of the time-series ultrasound images (i.e., on every frame) or may be performed on some of the time-series ultrasound images (on some frames).

Figures 5A, 5B:
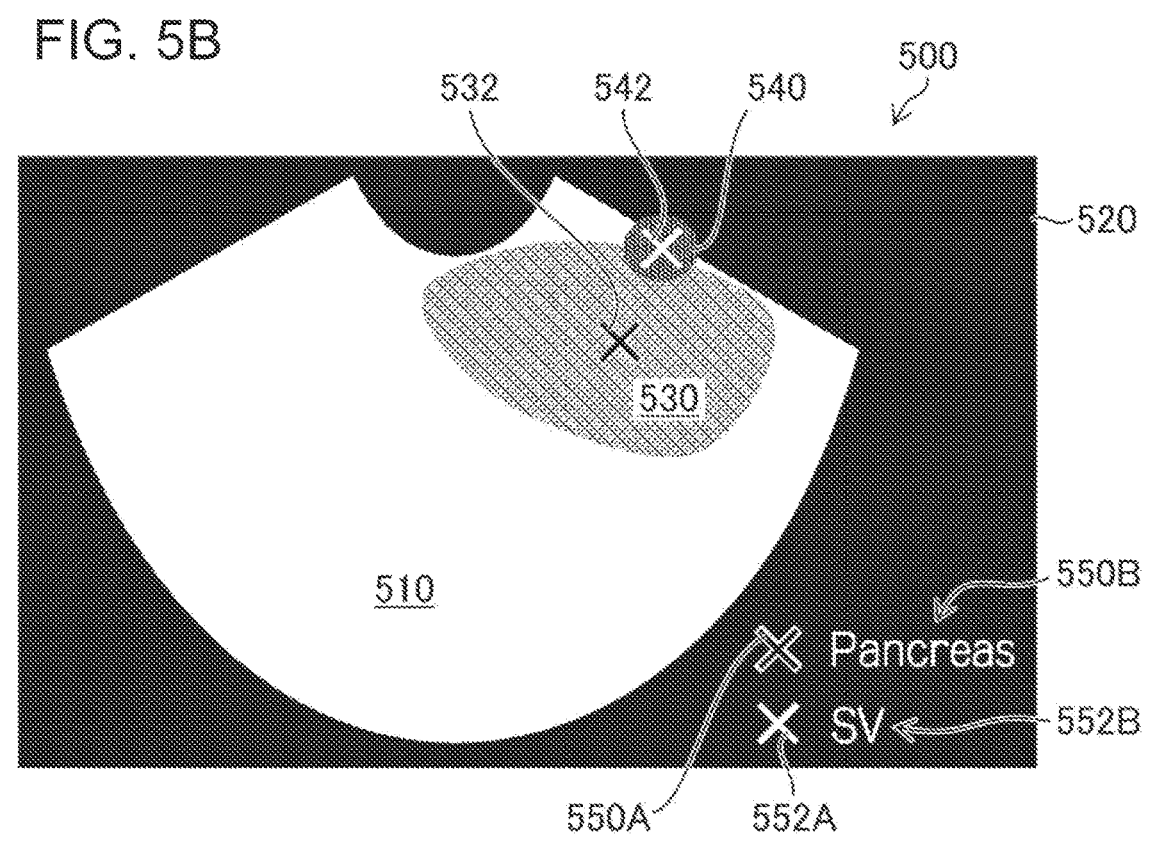
FIGS. 5A and 5B are views illustrating an example of superimposed display of position information and type information.

FIGS. 5A and 5B are views illustrating an example of superimposed display of the position information and the type information. In FIG. 5A, the pancreas 530 (region of interest) and the splenic vein 540 (region of interest) are detected (recognized) in an ultrasound image, and a geometric shape 532 and a geometric shape 542 (geometric shapes, position information) indicating the positions of the regions of interest are displayed superimposed on the inside of an image signal display area 510 (image signal display area, ultrasound image) on a display screen 500. Further, a text 550B ("Pancreas", type information) and a text 552B ("SV (Splenic Vein)", type information) indicating the names of the regions of interest are displayed superimposed on an area 520 outside the image signal display area 510. In addition, the same geometric shapes as the geometric shapes 532 and 542 indicating the position information are displayed in the area 520 as a legend 550A and a legend 552A (type information) alongside the texts 550B and 552B, respectively. Accordingly, the display control unit 112 associates the position information and the type information with each other.

FIG. 5B illustrates a state in which the positions of the regions of interest (the pancreas 530 and the splenic vein 540) have changed in the ultrasound image with the passage of time after the state illustrated in FIG. 5A (or with the passage of time and the change in observation position or direction due to the operation of the ultrasound scope 10). In this state, the display control unit 112 (processor) changes the positions at which the geometric shape 532 and the geometric shape 542 (position information) are to be displayed in accordance with the change in the positions of the regions of interest over time, while keeping the positions at which the texts 550B and 552B (type information) are to be displayed regardless of the change in the positions of the regions of interest over time.

In the display style illustrated in FIGS. 5A and 5B, a geometric shape (position information) indicating the position of a region of interest can support the user's observation. Since a simple geometric shape (cross) is displayed as the position information, the screen display is less likely to interfere with observation than when the name itself of an organ or the like is displayed in text. In addition, if the position of a region of interest has greatly changed on the screen over time, only the geometric shape (position information) moves, whereas the position of the text (type information) is maintained. This allows the user to easily grasp the type of the region of interest.

Figure 6A:
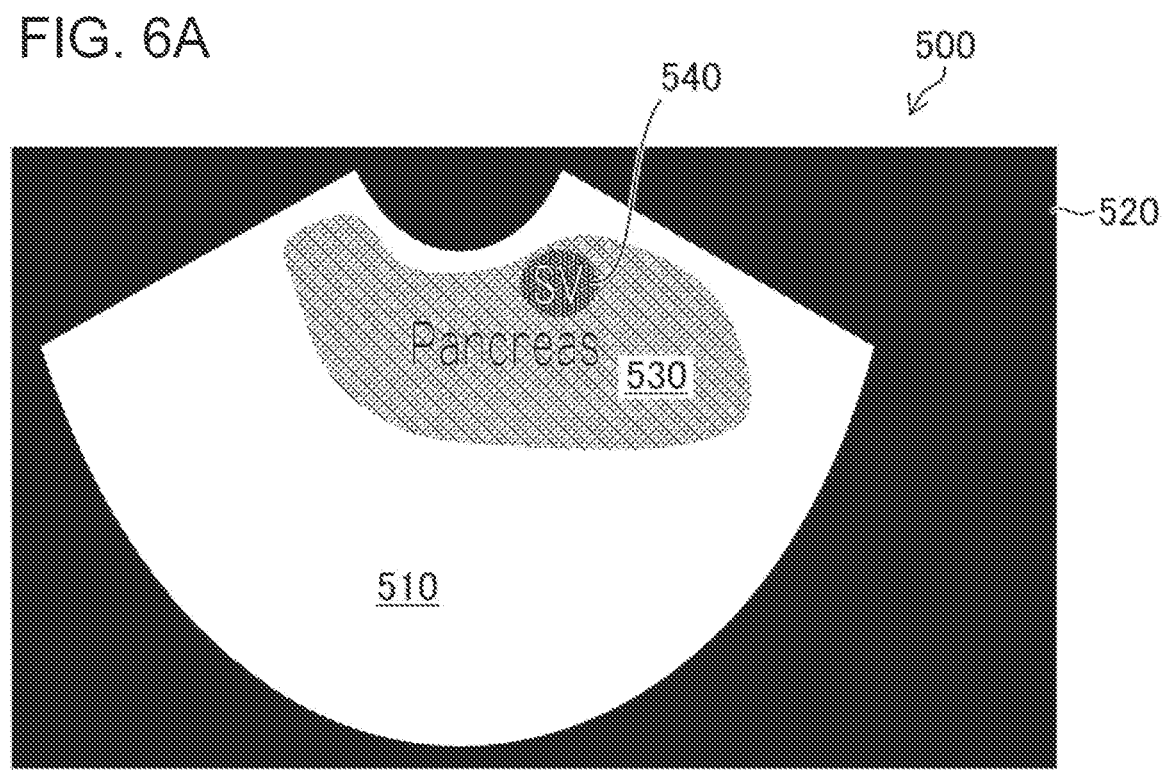
FIGS. 6A and 6B are views illustrating a comparative example of superimposed display of the position information and the type information.
Figure 6B:
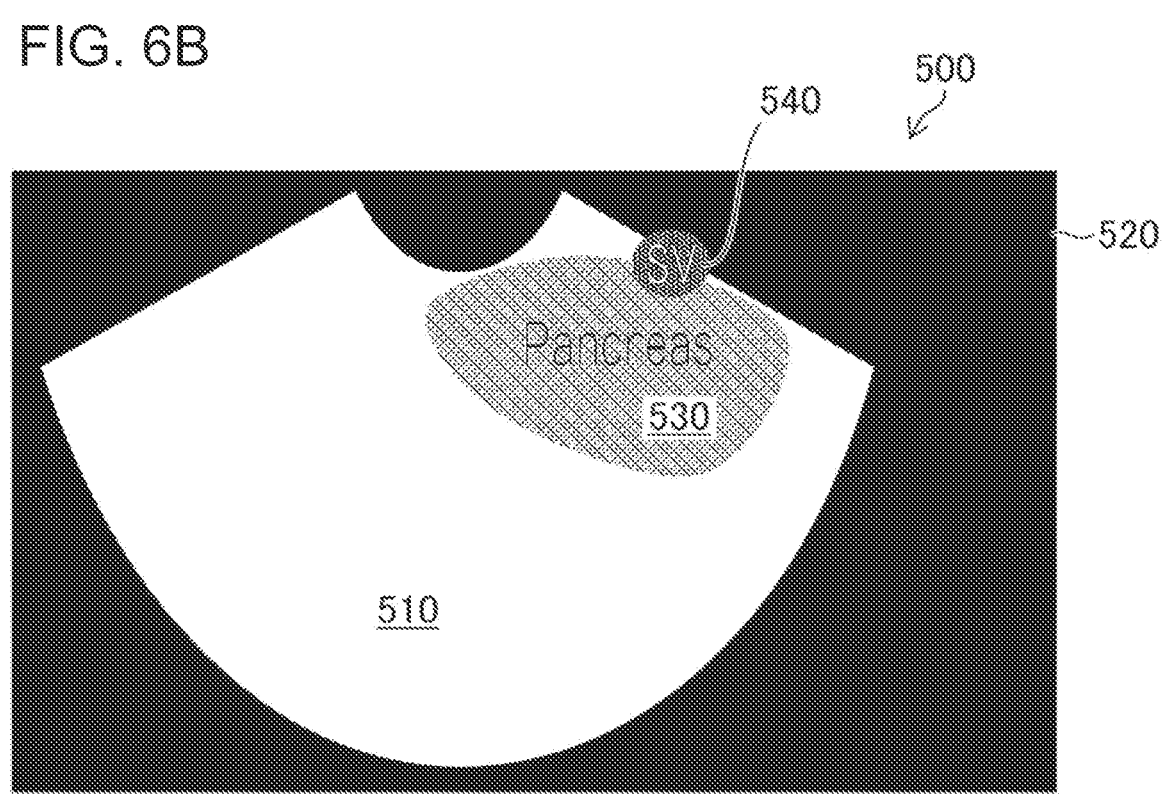

FIGS. 6A and 6B are views illustrating a comparative example of superimposed display of the position information and the type information, and illustrate a change with time. In the comparative example illustrated in FIGS. 6A and 6B, both the position information and the type information are represented by text, and the display positions of these pieces of information are changed with a change in the positions of the regions of interest. Thus, the screen display is more likely to interfere with observation than in the display style according to the present invention such as that in FIGS. 5A and 5B.

Figures 7, 8:
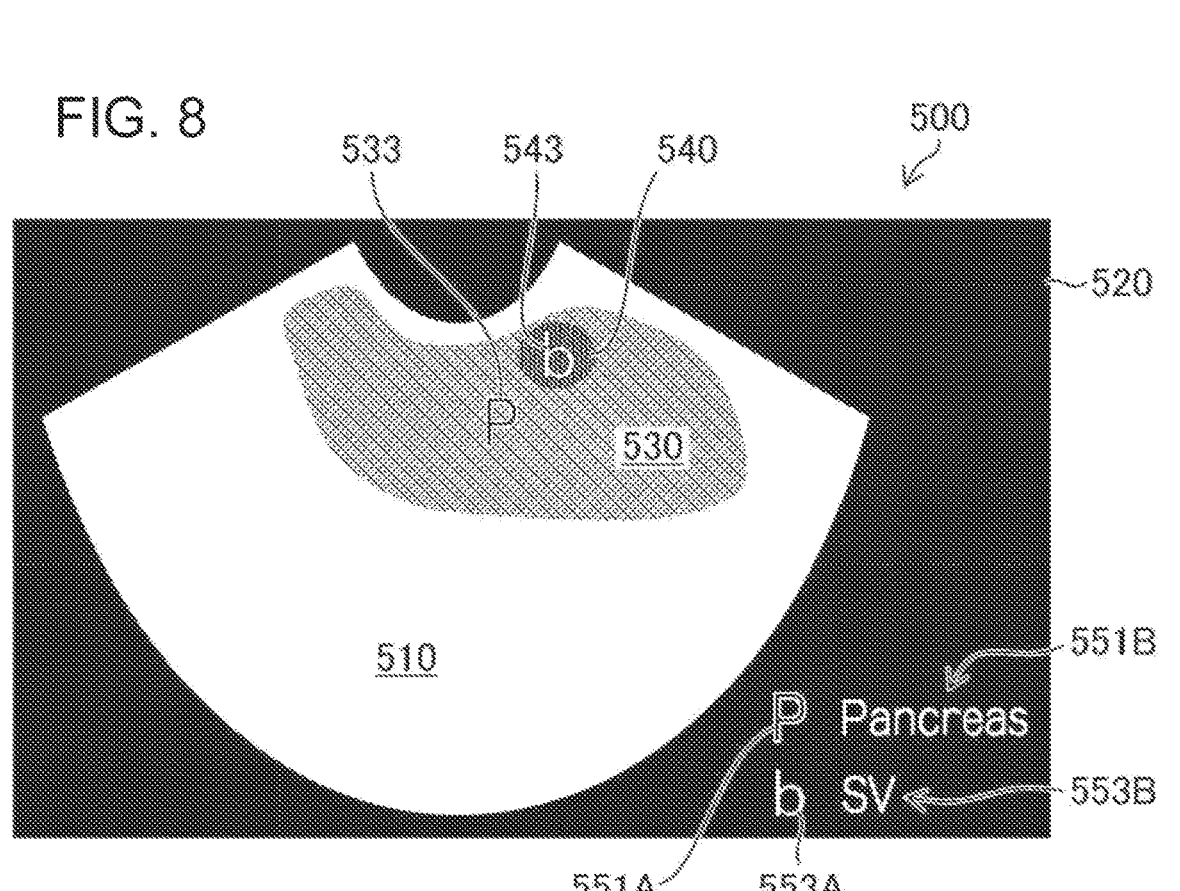
FIG. 7 is a view illustrating another example of superimposed display of the position information and the type information.
FIG. 8 is a view illustrating still another example of superimposed display of the position information and the type information.

FIG. 7 is a view illustrating another example of superimposed display of the position information and the type information. In the example illustrated in FIG. 7, the shape of a symbol indicating the position information is set in accordance with the type of the region of interest (the color of the symbol may be set in accordance with the type of the region of interest in addition to or instead of the shape of the symbol). Specifically, the display control unit 112 displays a geometric shape 532 (x-shaped cross) constituted by line segments extending in oblique directions as the position information of the pancreas 530, and displays a symbol 542A (plus-shaped cross) constituted by line segments in horizontal and vertical directions as the position information of the splenic vein 540. Further, the display control unit 112 displays these symbols as the legend 550A and a legend 552C (type information) alongside the texts 550B and 552B, respectively. The user gazes at an ultrasound image most of the time during an examination or observation, and it may be difficult for the user to move their line of sight to the outside of the image area (the outside of the image signal display area 510 or the area 520). Even in this case, as illustrated in FIG. 7, the shape or the like of a symbol indicating the position information is set in accordance with the type of a region of interest, thus allowing the user to easily grasp the type of the region of interest by checking the symbol displayed as the position information. The user can perform an operation of setting the shape and color of a symbol through a screen such as that in FIG. 4. The display control unit 112 can determine a display style in accordance with the user operation.

FIG. 8 is a view illustrating still another example of superimposed display of the position information and the type information. In the examples described above with reference to FIGS. 5A, 5B, and 7, an X-shaped cross or a plus-shaped cross is displayed as a symbol indicating the position information. In the example illustrated in FIG. 8, however, the display control unit 112 displays a geometric shape 533 (position information) indicating the initial of "Pancreas", namely, P, and a geometric shape 543 (position information) indicating the initial of "blood vessel", namely, b. Further, the display control unit 112 displays these symbols as a legend 551A and a legend 553A (type information) alongside the texts 551B and 553B (type information), respectively. This display allows the user to easily grasp the type of a region of interest by checking a symbol displayed as the position information.

Figure 9:
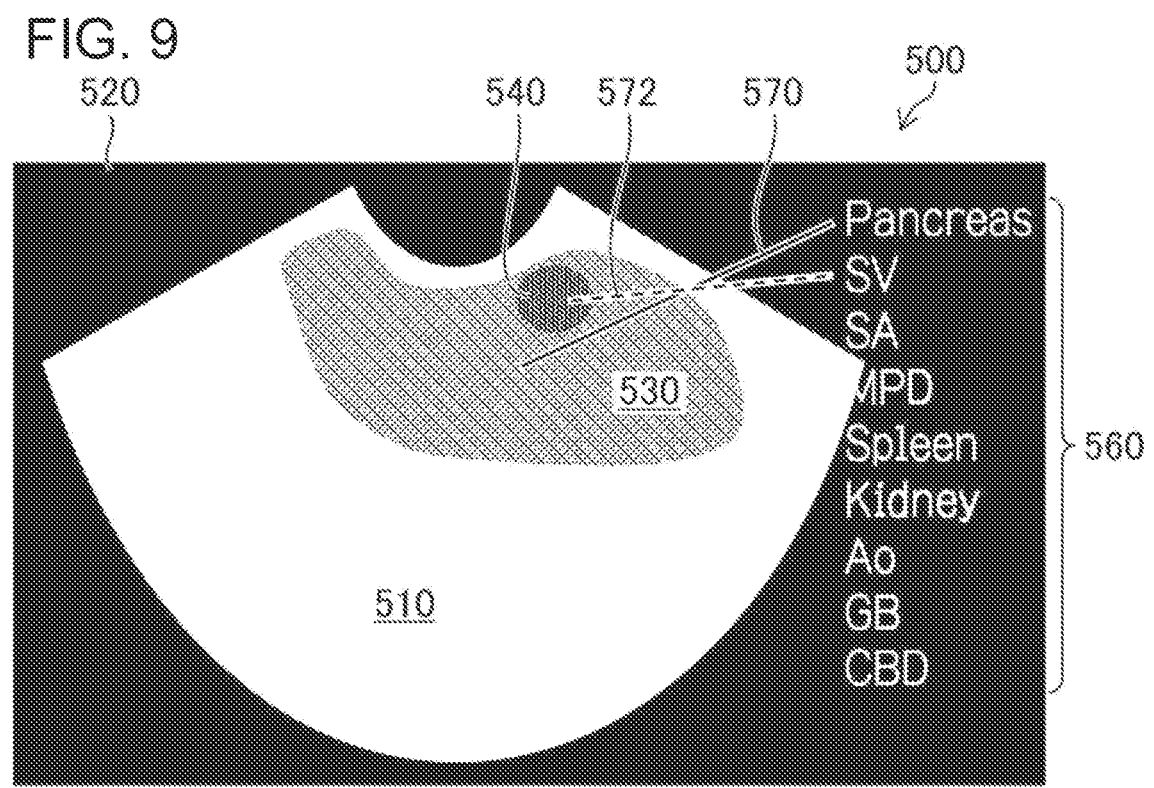
FIG. 9 is a view illustrating still another example of superimposed display of the position information and the type information.

FIG. 9 is a view illustrating still another example of superimposed display of the position information and the type information. In the display of the type information only for an actually detected region of interest, the displayed text may change as the type of the detected region of interest changes over time, which may disturb the user. In the example illustrated in FIG. 9, the display control unit 112 displays a list of types of regions of interest recognizable in the region-of-interest recognition process in an area 520 as text 560 (type information). The "type of region of interest recognizable in the region-of-interest recognition process" can be determined in accordance with the type or configuration of the endoscope system (such as an ultrasonic endoscope or an optical endoscope, an upper endoscope or a lower endoscope, or normal light or special light as the observation light, for example). Further, the display control unit 112 causes line segments 570 and 572 (line segments, leader lines) each having one endpoint at the position of the region of interest (the pancreas 530 and the splenic vein 540) and the other endpoint at the position of the text 560 (type information) to be displayed as the position information. The display control unit 112 may cause the line segments 570 and 572 to be displayed with different line types, as illustrated in FIG. 9. In addition to and/or instead of changing the line type, the display control unit 112 may change the line color (the same applies to FIGS. 10 and 11 described below).

This display allows the user to find the organ name (the type information of the region of interest) by tracing each line segment. Thus, the user can easily associate the screen of an ultrasound image with the organ names. The user can perform a setting operation for displaying a list or displaying line segments through a screen such as that in FIG. 4, for example. The display control unit 112 can determine a display style in accordance with the user operation.

Figure 10:
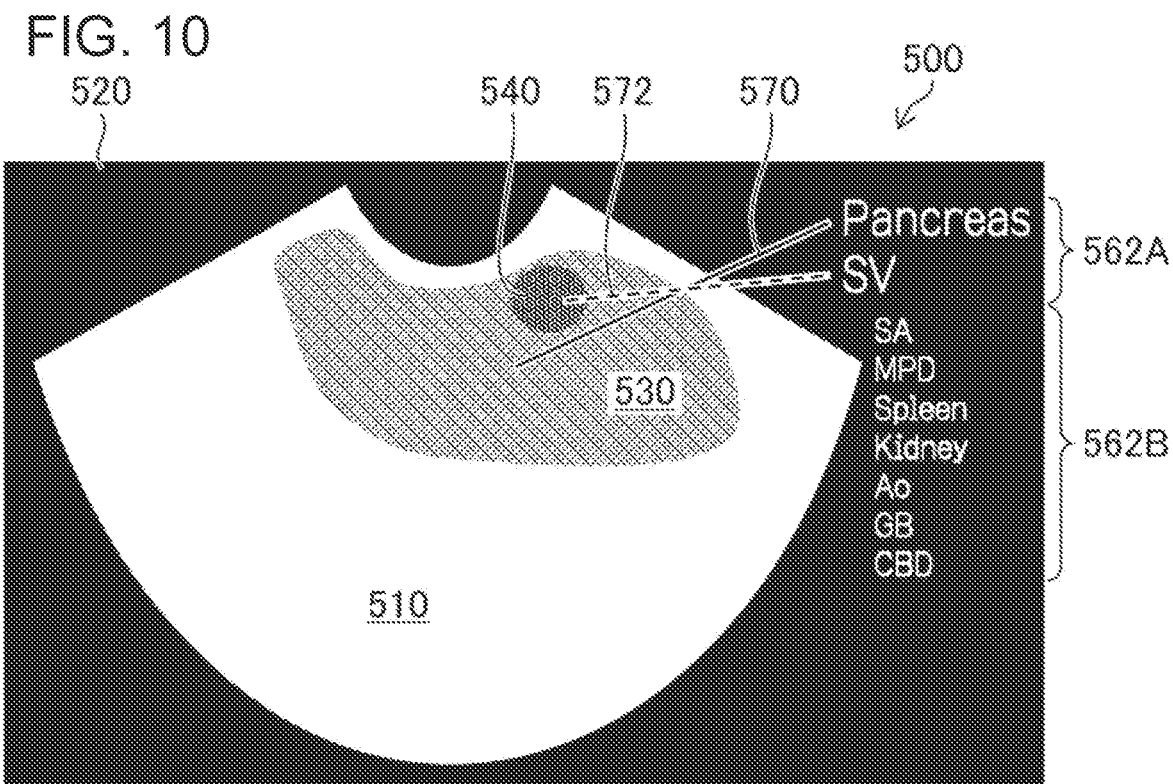
FIG. 10 is a view illustrating still another example of superimposed display of the position information and the type information.

FIG. 10 is a view illustrating still another example of superimposed display of the position information and the type information. In the example illustrated in FIG. 10, the display control unit 112 causes type information indicating a region of interest that is not actually recognized among regions of interest recognizable in the region-of-interest recognition process to be displayed with a lower notification level (second notification level) than the notification level (first notification level) for type information indicating a region of interest that is actually recognized. Specifically, the display control unit 112 causes "Pancreas" and "SV" corresponding to the pancreas 530 and the splenic vein 540 (regions of interest that are actually recognized) to be displayed in text 562A and causes the other regions of interest (regions of interest that are not actually recognized) to be displayed in text 562B smaller than the text 562A to make the notification level (second notification level) for the text 562B lower than the notification level (first notification level) for the text 562A.

Figure 11:
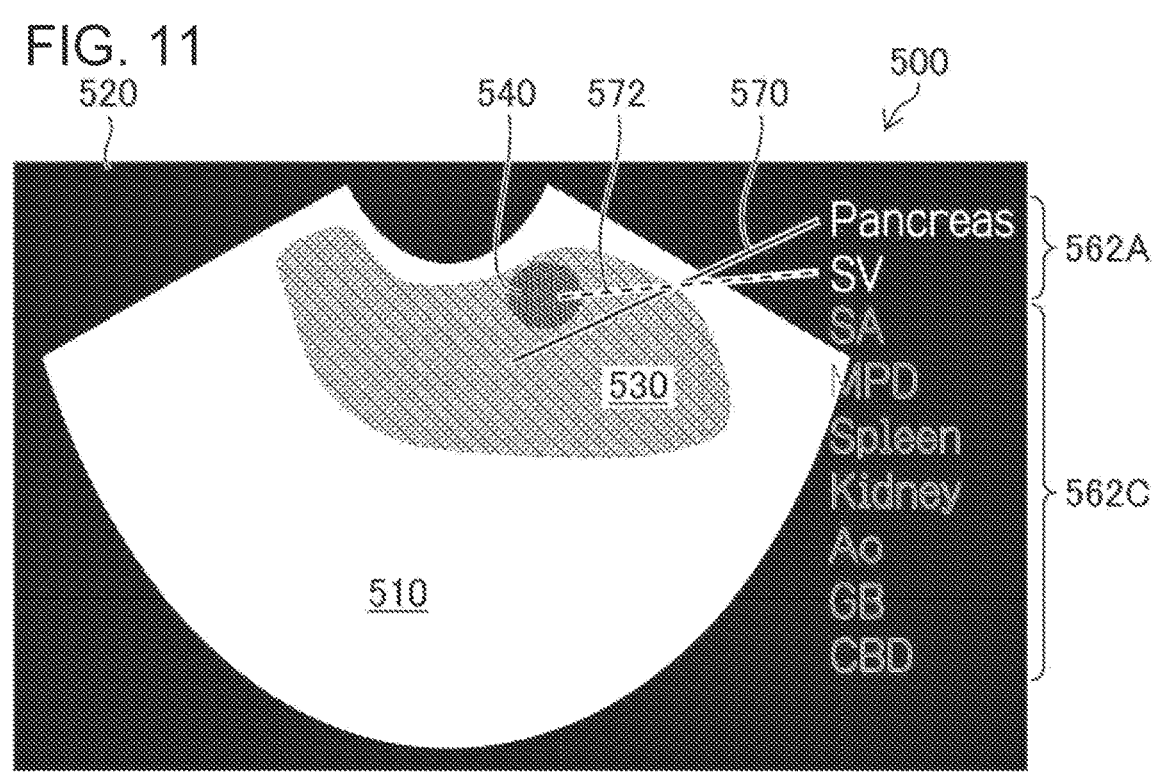
FIG. 11 is a view illustrating still another example of superimposed display of the position information and the type information.

FIG. 11 is a view illustrating still another example of superimposed display of the position information and the type information (another method for making the second notification level lower than the first notification level). In the example illustrated in FIG. 11, the display control unit 112 causes "Pancreas" and "SV" corresponding to the pancreas 530 and the splenic vein 540 to be displayed in the text 562A and causes the other regions of interest (regions of interest that are not actually recognized) to be displayed in grayed out text 562C to make the notification level (second notification level) for the text 562C lower than the notification level (first notification level) for the text 562A.

The display control unit 112 can use, as a method for reducing the notification level, any method other than that in the example illustrated in FIG. 10 or 11, such as reducing the thickness of text, increasing the transparency of the color of text, or reducing the lightness of the color of text. The display control unit 112 may use a combination of these methods. In the endoscope system 2, the notification described above can increase the visibility of a region of interest that is actually recognized. The user can perform setting to reduce the notification level through a screen such as that in FIG. 4, for example. The display control unit 112 can determine a display style in accordance with the user operation.

Change of Display in Accordance with Characteristics of Anatomical Region

Some anatomical regions (regions of interest) are required to be always displayed in text on an ultrasonic endoscope image. For example, the pancreas is a main organ to be observed with an ultrasonic endoscope, and is also an organ that is likely to be overlooked since the boundary with the surrounding tissue is unclear. It is therefore preferable that text be displayed on the screen for the pancreas to allow the user to easily grasp the position of the pancreas at all times. By contrast, the splenic vein (SV) is a blood vessel used as a basis for determining which portion of an endoscopic ultrasound image currently being viewed is displayed, and thus does not need to be always presented to the user. Since the splenic vein may be displayed in a very small size depending on the scene, a region of the splenic vein is not preferably hidden by a superimposed geometric shape.

Figure 12:
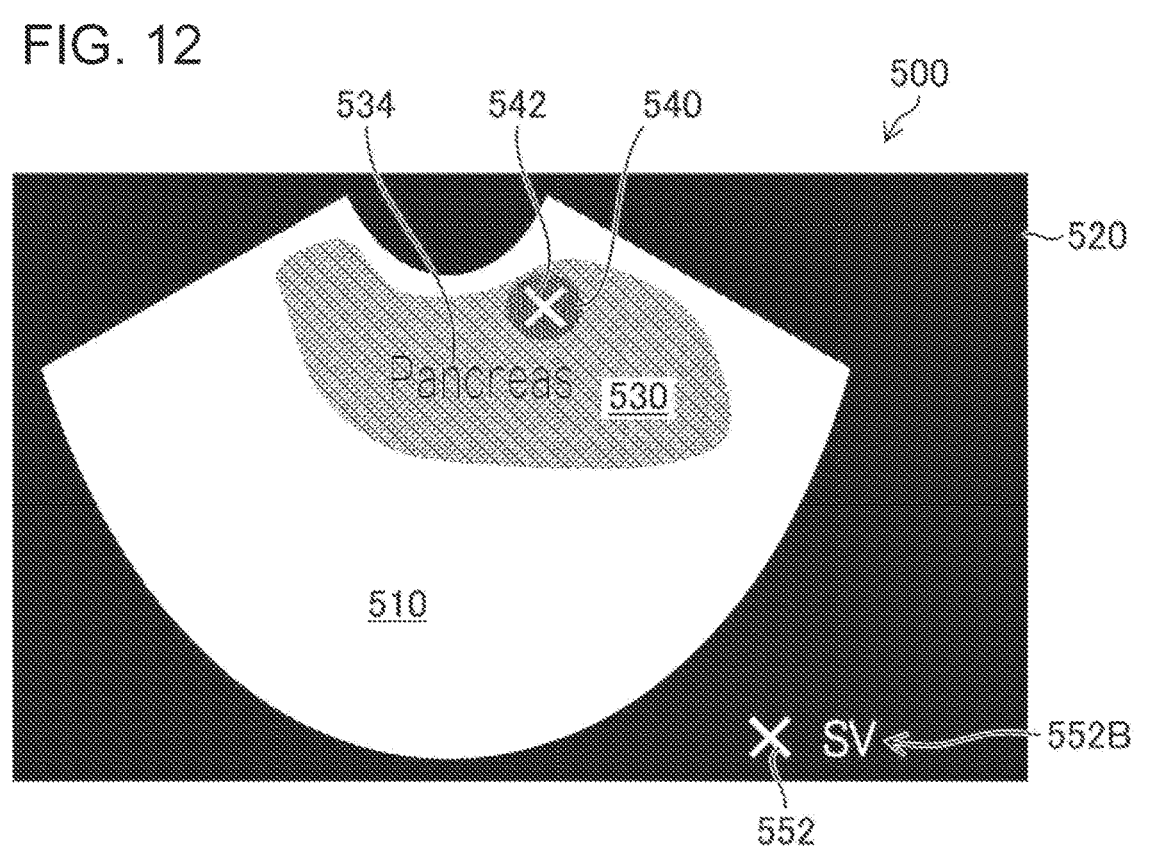
FIG. 12 is a view illustrating an example of setting the style of screen display in accordance with characteristics of an anatomical region.

Accordingly, in the first embodiment, the style of screen display may be set in accordance with the characteristics of the anatomical region. Specifically, the display control unit 112 may set the type of information to be displayed or whether to change the display position of the information as the position of the region of interest changes over time, in accordance with the type of the region of interest (the characteristics of the anatomical region). FIG. 12 illustrates an example of such screen display. The display control unit 112 causes a text 534 (position information, type information) to be displayed superimposed on the pancreas 530, and causes the geometric shape 542 (position information) to be displayed superimposed on the splenic vein 540. The display control unit 112 further causes a legend 552 (type information) and the text 552B ("SV"; type information) to be displayed side by side in the area 520. In the example in FIG. 12, the display control unit 112 causes the display positions of the text 534 and the geometric shape 542 to change as the positions of the regions of interest (the pancreas 530 and the splenic vein 540) in the ultrasound image change with time, while maintaining the display positions of the legend 552 and the text 552B regardless of a change in the position of the region of interest. That is, in the first embodiment, the display control unit 112 can cause the display position of not only the position information but also the type information of some regions of interest (the pancreas 530 in the example in FIG. 12) to change as the display positions of the regions of interest change with time, and can maintain the display position of the type information of the other regions of interest (the splenic vein 540 in the example in FIG. 12) regardless of a change in the display positions of the regions of interest with time. This makes it possible to provide an appropriate notification in accordance with the type of a region of interest (the characteristics of an anatomical region).

The user can perform an operation of setting the style of screen display in accordance with the characteristics of an anatomical region through a screen such as that in FIG. 4. The display control unit 112 can determine a display style in accordance with the user operation.

As described above, the endoscope system according to the first embodiment can provide an appropriate notification of a recognition result of a region of interest.

Applications to Other Medical Images

In the first embodiment described above, a description has been given of recognition using an ultrasonic endoscopic image, which is one aspect of a medical image (image for medical use). However, the medical image processing apparatus, the endoscope system, the medical image processing method, and the medical image processing program according to the present invention are also applicable to the use of medical images other than an ultrasonic endoscopic image, such as an ultrasound image acquired by an ultrasound apparatus (such as a body-surface endoscope apparatus) other than an endoscope and an endoscopic image acquired by an optical endoscope apparatus that captures an image of a subject by using white light and/or special light.

While an embodiment and other examples of the present invention have been described, the present invention is not limited to the aspects described above, and various modifications may be made.

REFERENCE SIGNS LIST 2 endoscope system
10 ultrasound scope
12 ultrasonic processor device
14 endoscope processor device
16 light source device
18 monitor
20 insertion section
20*a* longitudinal axis
22 handheld operation section
24 universal cord
26 ultrasonic connector
28 endoscope connector

16

30 light source connector
32 tube
34 tube
36 air/water supply button
38 suction button
42 angle knob
44 treatment tool insertion port
50 tip main body
52 bending part
54 soft part
62 ultrasound probe
64 balloon
70 water supply tank
72 suction pump
100 transmitting/receiving unit
102 image generation unit
104 CPU
106 region-of-interest recognition unit
110 communication control unit
112 display control unit
118 memory
120 recording unit
500 display screen
510 image signal display area
520 area
530 pancreas
532 geometric shape
533 geometric shape
534 text
540 splenic vein
542 geometric shape
543 geometric shape
550B text
551B text
552B text
553B text
560 text
562A text
562B text
562C text
570 line segment
572 line segment
S100 to S170 step of medical image processing method

What is claimed is:

1. A medical image processing apparatus comprising a processor configured to execute:
an image acquisition process for sequentially acquiring time-series medical images;
a region-of-interest recognition process for recognizing a position and a type of a region of interest from the medical images; and
a display control process for causing a display device to display position information indicating the position of the region of interest and type information indicating the type of the region of interest such that the position information and the type information are superimposed on the medical images, wherein
the processor is configured to, in the display control process, change a position at which the position information is to be displayed in accordance with a change in the position of the region of interest over time, and maintain a position at which the type information is to be displayed regardless of a change in the position of the region of interest over time, cause a geometric shape to be displayed as the position information at the position of the region of interest within an image signal display area in the medical images, and cause a same geometric shape as the geometric shape indicating the position information to be displayed alongside the type information in an outside of the image signal display area.

2. The medical image processing apparatus according to claim 1, wherein the processor is configured to, in the display control process, cause a text indicating the type of the region of interest to be displayed as the type information.

3. The medical image processing apparatus according to claim 1, wherein the processor is configured to cause a geometric shape or a text set in accordance with the type of the region of interest to be displayed as the position information.

4. The medical image processing apparatus according to claim 1, wherein the processor is configured to, in the display control process, cause the position information to be displayed in association with the type information.

5. The medical image processing apparatus according to claim 1, wherein the processor is configured to, in the display control process, cause a line segment having one endpoint at the position of the region of interest and another endpoint at a position of the type information to be displayed as the position information.

6. The medical image processing apparatus according to claim 5, wherein the processor is configured to cause the line segment to be displayed as the position information, in a state where at least one of a line type and a line color is changed according to the type information.

7. The medical image processing apparatus according to claim 1, wherein the processor is configured to, in the display control process, cause the type of the region of interest recognized in the region-of-interest recognition process to be displayed as the type information.

8. The medical image processing apparatus according to claim 1, wherein the processor is configured to, in the display control process, cause the type of the region of interest recognizable in the region-of-interest recognition process to be displayed as the type information.

9. The medical image processing apparatus according to claim 8, wherein the processor is configured to cause the type information indicating a region of interest that is not actually recognized among regions of interest recognizable in the region-of-interest recognition process to be displayed with a second notification level lower than a first notification level for the type information indicating a region of interest that is actually recognized in the region-of-interest recognition process.

10. An endoscope system comprising:

the medical image processing apparatus according to claim 1;

an endoscope to be inserted into a subject, the endoscope comprising an imaging unit configured to sequentially capture the medical images; and the display device.

11. The endoscope system according to claim 10, wherein the endoscope is an ultrasonic endoscope configured to acquire ultrasound images of the subject as the medical images.

12. A medical image processing method executed by a medical image processing apparatus comprising a processor, the processor being configured to execute:

an image acquisition step of sequentially acquiring time-series medical images;

a region-of-interest recognition step of recognizing a position and a type of a region of interest from the medical images; and a display control step of causing a display device to display position information indicating the position of the region of interest and type information indicating the type of the region of interest such that the position information and the type information are superimposed on the medical images, wherein the processor is configured to, in the display control step, change a position at which the position information is to be displayed in accordance with a change in the position of the region of interest over time, and maintain a position at which the type information is to be displayed regardless of a change in the position of the region of interest over time, cause a geometric shape to be displayed as the position information at the position of the region of interest within an image signal display area in the medical images, and cause a same geometric shape as the geometric shape indicating the position information to be displayed alongside the type information in an outside of the image signal display area.

13. A non-transitory, computer-readable tangible recording medium storing a program for causing, when read by a computer, the computer to execute the medical image processing method according to claim 12.

\* \* \* \* \*